US00PP33615P2

(12) United States Plant Patent
Hartman

(10) Patent No.: US PP33,615 P2
(45) Date of Patent: Nov. 2, 2021

(54) CALADIUM PLANT NAMED 'RUF 1522-3'

(50) Latin Name: ***Caladium* X *hortulanum***
Varietal Denomination: RUF 1522-3

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/013,809

(22) Filed: Sep. 7, 2020

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'RUF 1522-3', characterized by its compact and mounding plant habit; dense and bushy appearance; vigorous growth habit and rapid growth rate; lance-type leaves that are dark red in color with dark green-colored margins; and petioles that are tannish pink in color with greenish brown-colored stripes, streaks and tessellations.

6 Drawing Sheets

Figure 1:
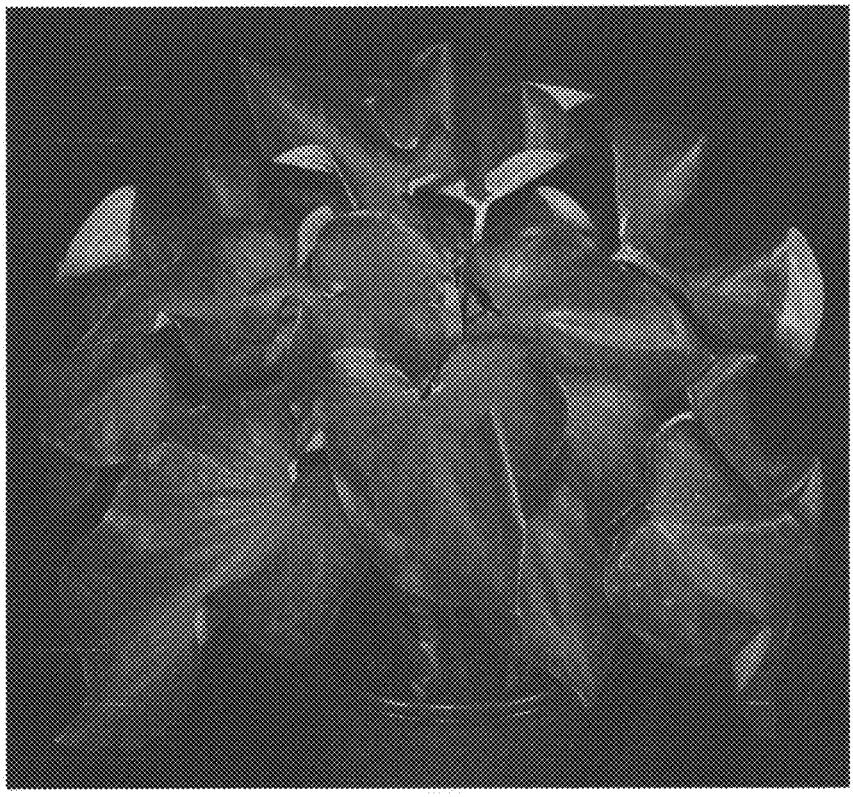

Botanical designation: *Caladium* X *hortulanum*.
Cultivar denomination: 'RUF 1522-3'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'RUF 1522-3'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium* X *hortulanum* 'Florida Red Ruffles', disclosed in U.S. Plant Pat. No. 13,136, as the female, or seed, parent with *Caladium* X *hortulanum* 'Frieda Hemple', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2010.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'RUF 1522-3'. These characteristics in combination distinguish 'RUF 1522-3' as a new and distinct *Caladium* plant:

1. Compact and mounding plant habit; dense and bushy appearance.
2. Vigorous growth habit and rapid growth rate.
3. Lance-type leaves that are dark red in color with dark green-colored margins.
4. Petioles that are tannish pink in color with greenish brown-colored stripes, streaks and tessellations.

Plants of the new *Caladium* differ primarily from plants of the female parent, 'Florida Red Ruffles', in the following characteristics:

1. Plants of the new *Caladium* and 'Florida Red Ruffles' differ in leaf color as leaves of the new *Caladium* are dark red in color with dark green-colored margins whereas leaves of 'Florida Red Ruffles' are dark red in color with lighter green-colored borders. Under full sunlight conditions, leaves of plants of the new *Caladium* are darker red than leaves of plants of 'Florida Red Ruffles'.

2. Plants of the new *Caladium* have not been observed to initiate and develop inflorescences whereas plants of 'Florida Red Ruffles' initiate and develop inflorescences freely.
3. When grown under field conditions, plants of the new *Caladium* are more tolerant (less susceptible) to *Pythium* Root Rot than plants of 'Florida Red Ruffles'.

Plants of the new *Caladium* differ primarily from plants of the male parent, 'Frieda Hemple', in the following characteristics:

1. Plants of the new *Caladium* have lance type leaves whereas plants of 'Frieda Hemple' have fancy type leaves.
2. Plants of the new *Caladium* and 'Frieda Hemple' differ in leaf color as leaves of the new *Caladium* are dark red in color with dark green-colored margins whereas leaves of 'Frieda Hemple' are bright red in color with lighter green-colored borders.
3. Plants of the new *Caladium* and 'Frieda Hemple' differ in leaf petiole color as leaf petioles of the new *Caladium* are tannish pink in color with greenish brown-colored stripes, streaks and tessellations whereas leaf petioles of 'Frieda Hemple' are tannish pink in color with dense black-colored stippling and streaks.
4. When grown under field conditions, plants of the new *Caladium* are more tolerant (less susceptible) to *Pythium* Root Rot than plants of 'Frieda Hemple'.

Plants of the new *Caladium* can be compared to plants of *Caladium* X *hortulanum* 'Red Frills', not patented. In side-by-side comparisons, plants of the new *Caladium* differ primarily from plants of 'Red Frills' in the following characteristics:

1. Plants of the new *Caladium* and 'Red Frills' differ in leaf color as leaves of the new *Caladium* are dark red in color with dark green-colored margins whereas leaves of 'Red Frills' are duller red in color with lighter green-colored borders and occasionally random pink-colored spots.
2. Plants of the new *Caladium* and 'Red Frills' differ in leaf petiole color as leaf petioles of the new *Caladium* are tannish pink in color with greenish brown-colored stripes, streaks and tessellations whereas leaf petioles of 'Red Frills' are tannish pink in color with greenish brown-colored streaks and tessellations.

Plants of the new *Caladium* can also be compared to plants of *Caladium* X *hortulanum* 'Heart's Delight', disclosed in U.S. Plant Pat. No. 23,992. In side-by-side comparisons, plants of the new *Caladium* differ primarily from plants of 'Heart's Delight' in the following characteristics:

1. Plants of the new *Caladium* and 'Heart's Delight' differ in leaf color as leaves of the new *Caladium* are dark red in color with dark green-colored margins whereas leaves of 'Heart's Delight' have red-colored venation, greyed purple-colored interveinal areas and mottled light and dark green-colored borders.
2. Leaves of plants of the new *Caladium* have more rounded leaf lobes than plants of 'Heart's Delight' which are more hastate in shape.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'RUF 1522-3' in a container and grown in a shade house (tuber de-eyed).

Figure 2:
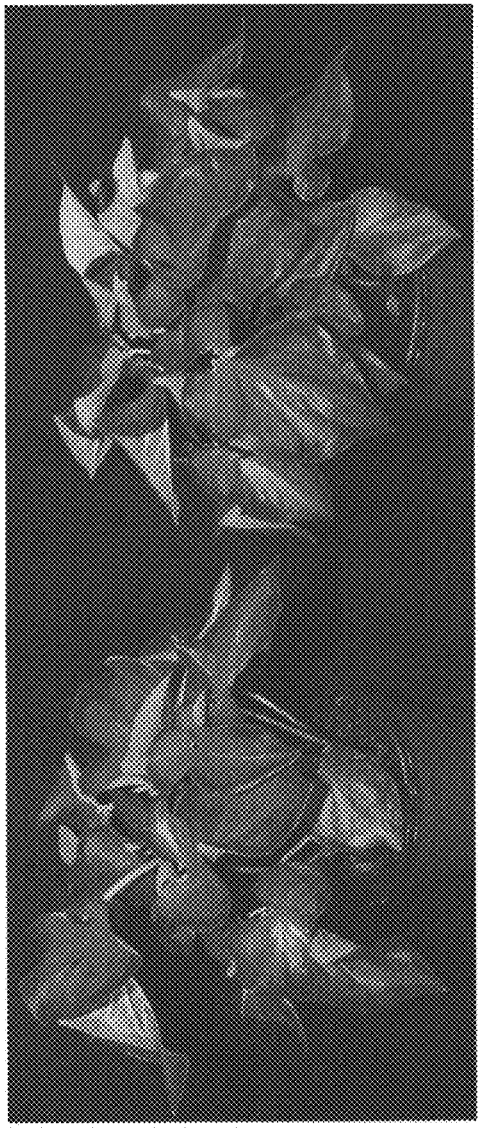
Figure 3:
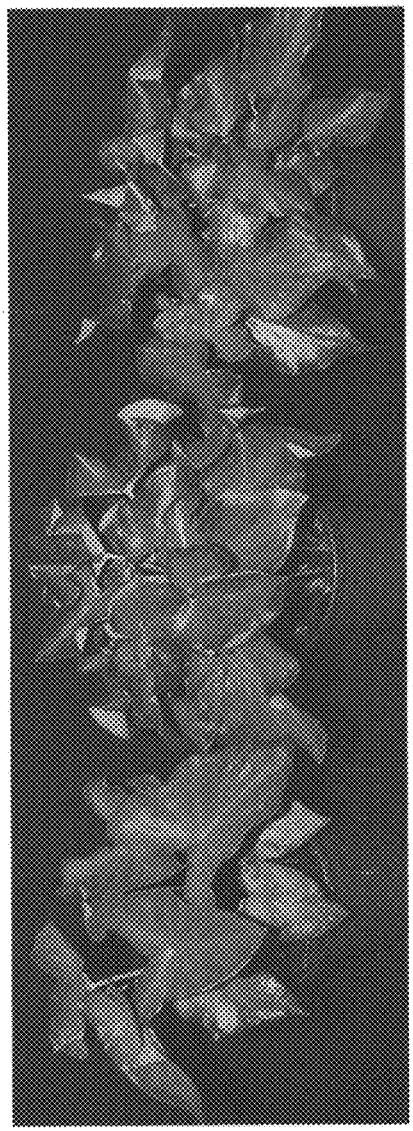

The photograph on the second sheet (FIG. 2) is a comparison view of typical plants of 'RUF 1522-3' grown in containers, the plant on the left has not had its tuber de-eyed and the plant on the right has had its tuber de-eyed prior to planting; the photograph on the third sheet (FIG. 3) is side perspective view of the female parent, 'Florida Red Ruffles' (left), 'RUF 1522-3' (center) and the male parent, 'Frieda Hemple' (right).

Figure 4:
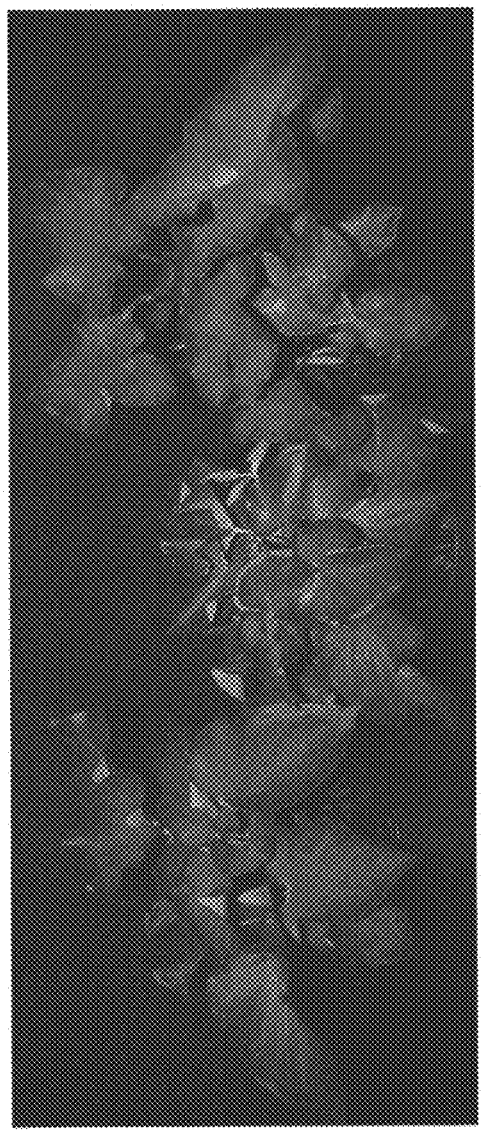

The photograph on the fourth sheet (FIG. 4) is a comparison view of typical potted plants of 'Red Frills' (left), 'RUF 1522-3' (center) and 'Heart's Delight' (right).

Figure 5:
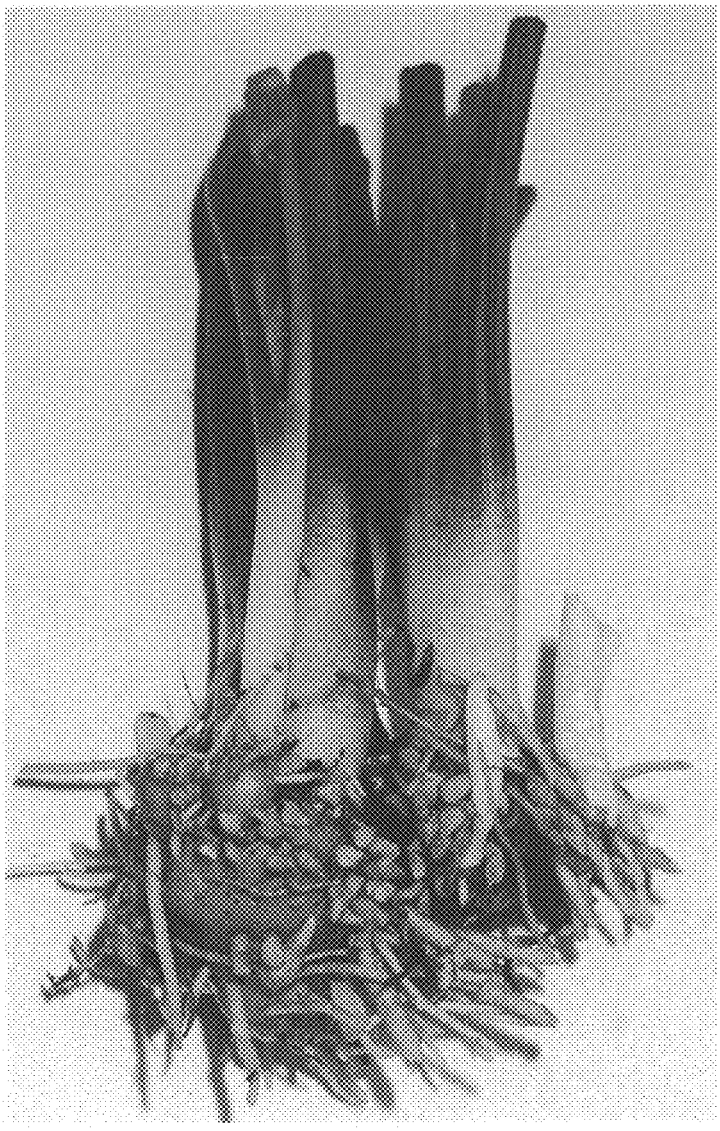

The photograph on the fifth sheet (FIG. 5) is a close-up view of typical freshly-harvested tubers with roots and leaf petioles of 'RUF 1522-3'.

Figure 6:
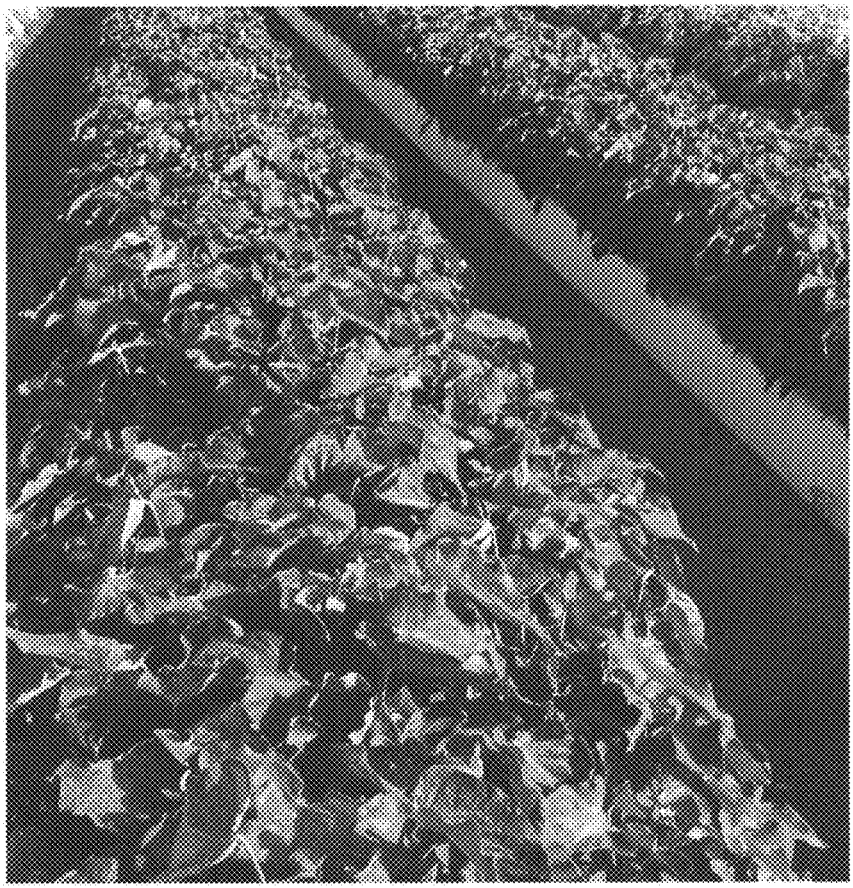

The photograph on the sixth sheet (FIG. 6) is a side perspective view of typical plants of 'RUF 1522-3' grown in an open production field.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were eight weeks old and plants grown in the outdoor nursery were seven months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'RUF 1522-3'.

Parentage:

*Female, or seed, parent.*—*Caladium* X *hortulanum* 'Florida Red Ruffles', disclosed in U.S. Plant Pat. No. 13,136.

*Male, or pollen, parent.*—*Caladium* X *hortulanum* 'Frieda Hemple', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic to irregular in shape. Height: About 2.5 cm.

Diameter: About 3.5 cm to 6.3 cm. Segment height: About 1.9 cm to 2.3 cm. Segment diameter: About 2.3 cm to 2.5 cm. Axillary bud shape: Roughly triangular. Texture: Thick, starchy; somewhat brittle. Color: Periderm, freshly-harvested: Close to 199B to 199C. Periderm, dried: Close to 200A to 200B. Epidermis: Close to 158D and N155C. Cortical tissue: Close to 8D. Axillary buds: Close to 36C and 36D. Root description: Thick, fleshy contractile roots with few lateral branches; color, close to N155D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Compact and mounding plant habit; dense and bushy appearance; vigorous growth habit and rapid growth rate; potted plants finish in saleable form in about five to six weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 37 cm to 39 cm.

*Plant height, from soil level to top of foliar plane, shade house-grown potted plants*.—About 25 cm to 28 cm.

*Plant diameter or spread, shade house-grown potted plants*.—About 38 cm to 43 cm.

*Number of shoots per plant, shade house-grown potted plants, tubers de-eyed*.—About four to five develop per #1 tuber.

*Number of shoots per plant, shade house-grown potted plants, tubers not de-eyed*.—About three to four develop per #1 tuber.

*Cataphylls, shade house-grown potted plants*.—Length: About 3.5 cm to 5 cm. Width: About 1.2 cm to 1.8 cm. Shape: Wedge-shaped. Apex: Acuminate or emarginate. Base: Sheathing the stem. Color: Outer surface: Close to 199A streaked, stippled and tessellated with close to 200A and 200B; color becoming closer to N199A with development. Inner surface: Close to N155C and N155D; colors and patterns on outer surface visible on inner surface.

Leaf description:

*Arrangement and type*.—Alternate; simple; lance-type.

*Length, shade house-grown potted plants*.—About 11 cm to 18 cm.

*Width, shade house-grown potted plants*.—About 9 cm to 15 cm; when flattened, about 9.4 cm to 15.5 cm.

*Shape*.—Ovate.

*Apex*.—Acute.

*Base*.—Sagittate of sagittate-peltate, cordate.

*Margin*.—Entire; wavy with broad undulations.

*Texture and luster, upper surface*.—Smooth, glabrous; leathery; dull sheen.

*Texture and luster, lower surface*.—Smooth, glabrous; slightly glaucous; dull sheen.

*Venation pattern*.—Pinnate and palmate.

*Color, shade house-grown potted plants*.—Fully developed leaves, upper surface: Background (interveinal areas) color: Close to 53A tinged with close to N186C, 183A and 139A with occasional random variable areas, close to 47A and speckles, close to 155C. Towards the margins: Close to 139A tinged with close to 147A; leaf edge, close to 183A. Basal notch: Close to 147C tinged with close to 187A and 187B. Midvein and lateral venation: Close to 53A. Fully developed leaves, lower surface: Background (interveinal areas) color: Close to 183A, 187C and 185A Towards the margins: Close to 191A tinged with close to 189A; leaf edge, close to 183A. Leaf attachment point: Close to 191A tinged with close to 187C. Midvein: Close to 195C or close to 182D flushed and streaked with close to 184B and 184C. Primary and secondary venation: Close to 194B and 195C may be tinged with close to 182D and flushed and streaked with close to 184B.

*Petioles*.—Aspect: Initially upright and straight and leaning outwardly with development; flexible. Length, shade house-grown potted plants: About 23 cm to 25.2 cm. Diameter, distally, shade house-grown potted plants: About 3 mm to 4 mm. Diameter, proximally, shade house-grown potted plants: About 3.5 mm to 6 mm. Texture and luster: Smooth, glabrous; dull to slightly glossy; just below the leaf junction, slightly glaucous. Color, shade house-grown potted plants: When developing and fully developed: Close to 199D tinged with close to 182D and 147C with stippling, streaks, stripes and tessellations of close to 200A tinged with close to 147A; just below the leaf junction, close to 199D tinged with close to 182D and 147C with stippling, streaks, stripes and tessellations of close to 200A tinged with close to 147A and flushed with close to 182C. Wing length, shade house-grown potted plants: About 3 cm to 4.5 cm. Wing diameter, shade house-grown potted plants: About 5 mm to 7 mm. Texture and luster, inner and outer surfaces: Smooth, glabrous; dull sheen. Wing color, shade house-grown potted plants: Outer surface: Close to 199A with stippling, streaks and tessellations of close to 200A and 200B. Inner surface: Close to N155D; colors and patterns on the outer surface are visible on the inner surface.

Inflorescence description: To date, inflorescence development has not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'RUF 1522-3' as illustrated and described.

* * * * *